(12) United States Patent
Sommer

(10) Patent No.: US 6,959,068 B1
(45) Date of Patent: Oct. 25, 2005

(54) COMPUTED TOMOGRAPHY APPARATUS

(75) Inventor: Andres Sommer, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/495,710

(22) Filed: Feb. 1, 2000

(30) Foreign Application Priority Data

Feb. 26, 1999 (DE) .................................. 199 08 494

(51) Int. Cl.[7] ........................................... G01N 23/00
(52) U.S. Cl. ........................... 378/20; 378/4; 378/208
(58) Field of Search ........................ 378/4, 19, 20, 378/205, 208, 209, 195, 196, 197, 198, 12

(56) References Cited

U.S. PATENT DOCUMENTS

| 3,803,417 | A | * | 4/1974 | Kok ............................ 378/189 |
| 4,942,597 | A | * | 7/1990 | Van Acker et al. ......... 378/197 |
| 5,448,607 | A | | 9/1995 | McKenna |
| 5,499,415 | A | | 3/1996 | McKenna |
| 5,638,419 | A | | 6/1997 | Ingwersen |
| 5,774,916 | A | * | 7/1998 | Kurhi ............................ 5/632 |
| 5,848,126 | A | * | 12/1998 | Fujita et al. ................ 378/195 |
| RE36,099 | E | * | 2/1999 | Gordon ........................ 378/20 |
| RE36,415 | E | * | 11/1999 | McKenna ....................... 378/4 |
| 6,003,174 | A | * | 12/1999 | Kantrowitz et al. ............ 5/601 |
| 6,031,888 | A | * | 2/2000 | Ivan et al. .................... 378/20 |
| 6,125,163 | A | * | 9/2000 | Barth et al. .................... 378/4 |
| 6,155,713 | A | * | 12/2000 | Watanabe .................... 378/197 |
| 6,212,251 | B1 | * | 4/2001 | Tomura et al. ................ 378/15 |

* cited by examiner

Primary Examiner—David V. Bruce
Assistant Examiner—Hoon Song
(74) Attorney, Agent, or Firm—Schiff Hardin LLP

(57) ABSTRACT

A computed tomography apparatus has a gantry with a measuring opening, with an x-ray source movable around the measuring opening for irradiating an examination area from different directions, a detector for registering corresponding sets of projection data, and at least one support table having a support plate. The gantry can be moved into a use position independently of the support table and the support table is fashioned such that the support plate extends through the measuring opening when the gantry assumes a use position.

6 Claims, 2 Drawing Sheets

COMPUTED TOMOGRAPHY APPARATUS

BACKGROUND OF THE INVENTION

1. Field of the Invention

The present invention is directed to a computed tomography apparatus of the type having a gantry with a measuring opening, an X-ray source movable around the measuring opening for irradiating an examination area from different directions, a detector for registering corresponding projections, and at least one support table having a support plate, with the gantry being movably fashioned such that it can be moved into at least one use position.

2. Description of the Prior Art

U.S. Pat. No. 5,448,607 and U.S. Pat. No. 5,499,415 describe computed tomography apparatuses of the above general type.

It has been determined that approximately 50 through 60% of the time spent at computed tomography apparatuses in hospitals at the moment is occupied by positioning the patient on the support table in a way appropriate for the respective examination. During that time, the computed tomography apparatus cannot be used for examinations, since the service personnel are occupied with waiting while the patient climbs onto the support table, which is firmly attached to the computed tomography apparatus and which is technically complicated, and the service personnel are then occupied with positioning the patient thereon.

In order to reduce such apparatus downtime it is known from the aforementioned patents to fashion the gantry and the support table such that they can be moved. Such a movable table, as the table of a conventional computed tomography apparatus, is provided with a longitudinally displaceable support plate that is attached to the movable pedestal of the support table. Additionally, a coupling mechanism, which enables a rigid connection of the support table with the gantry, is provided. This enables patients to be prepared without blocking use of the computed tomography apparatus but the overall technical outlay that is required is not less, and is perhaps greater, compared to a conventional computed tomography apparatus.

The same is true of the computed tomography apparatus known from German OS 195 05 276, which has a gantry, which is movable relative to a stationary support table and which, docked to the patient support table, can be adjusted relative to the support table by a drive unit.

SUMMARY OF THE INVENTION

An object of the present invention is to provide a computed tomography apparatus of the type described above which allows a technically simple way for preparing patients on the support table for examinations without blocking the computed tomography apparatus.

This object is achieved in accordance with the invention in a computed tomography apparatus wherein the gantry can be moved independently of the support table and that is preferably motor-driven, and wherein the support table, has a support plate with one end non-displaceably mounted cantilevered to a carrier, wherein an adjustment of the support plate is not required in order to place it into the measuring opening of the gantry. As a result, the gantry can be moved toward the other end of the support plate without any problems so that the support plate extends through the measuring opening of the gantry in the use position, and therefor the support table need not have a displaceable support plate nor a driving device for the support plate.

Thus, the support table can be constructed extremely simply, so that a number of support tables can be economically provided, enabling the preparation of a number of patients at the same time for an examination at the computed tomography apparatus.

In an embodiment of the invention, the carrier have a floor stand or a ceiling stand, but a floor stand is advantageous when the support table is movably fashioned according to a version of the invention, since, differing from the use of a ceiling stand, rails are then not necessary. The utilization of a ceiling stand, however, has the advantage that it usually represents a less disturbing impediment to personnel movement, and the placement of auxiliary devices, compared to a floor stand.

In another embodiment of the invention, the support table can be positioned relative to the gantry such that straight lines, generated by parallel projections of the longitudinal axis of the support plate and the system axis into a horizontal plane, for example, the floor of the examination room, are crossed (intersect) when the gantry is situated in a use position. In a simple way, it is therefore possible to achieve the equivalent of swivelling of a conventional support table without mechanical measures. Only the diameter of the measuring opening and the width of the support plate must be selected corresponding to a maximally desired extent of the swivel.

In a preferred embodiment of the invention the gantry can be moved in the direction of the system axis for volume scanning of the examination area with the support plate situated in the measuring opening. Therefore, it is possible to undertake spiral scans or sequence scans.

The movability of the gantry can be achieved in a particularly simple and precise way when it is movable on rails according to a version of the invention.

DESCRIPTION OF THE PREFERRED EMBODIMENTS

Figure 1:
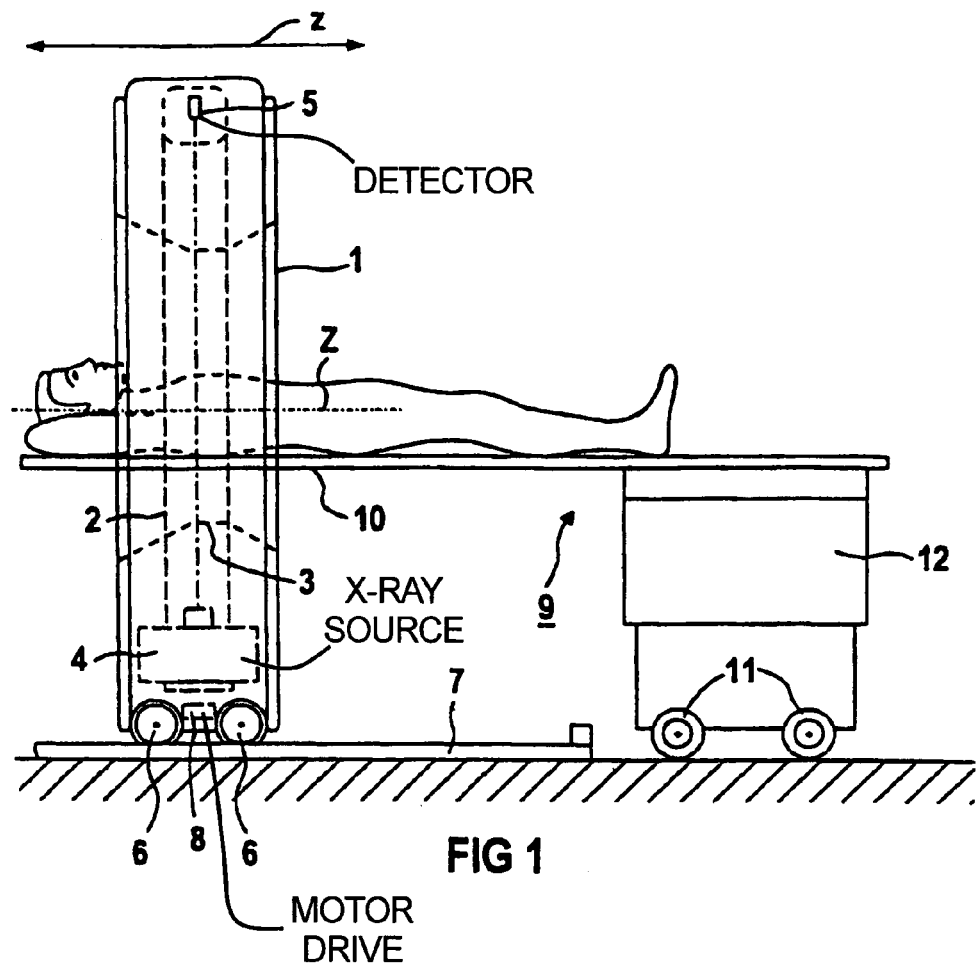
FIG. 1 is a side view of an inventive computed tomography apparatus.

FIG. 1 shows a computed tomography apparatus having a gantry 1 with a measuring opening 2, which is surrounded by a rotary ring 3 on which an x-ray source 4 and a curved detector 5 are mounted. The x-ray source 4 emits a fan-shaped x-ray bundle (not shown) that is incident on the detector 5, which is curved around the focus of the x-ray source 4 and which is formed by a series of individual detectors.

By means of rollers 6 on parallel rails (only one is visible in FIG. 1), the gantry 1 is movable in the direction of the double arrow z by a motor drive 8 (shown in broken lines in FIG. 1). This movement is independent of a support table 9 on which a support plate 10 for a patient to be examined is situated.

For producing computed tomographic images, the gantry 1 with the x-ray source 4 and the detector 5 is moved from a standby position (not shown) relative to the support table 9, into a use position in which the support plate 10 of the support table 9 extends through the measuring opening 2 of the gantry 1, as is necessary for producing computed tomographic images of the patient. For purposes of producing an image of a planar slice of the patient, the rotary ring 3 with the x-ray source 4 and the detector 5 is rotated around the system axis Z for the acquisition of a number of projection datasets with the x-ray source 4 irradiating the patient on the support plate 10 respectively from different directions. These projection datasets serve the purpose of reconstructing a tomogram in a known manner. During this data acquisition the gantry 1 remains stationary on the rails 7 and the support table 9 remains stationary on the wheels 11.

The gantry 1 can be moved into the use position, since the support plate 10 of the support table 9 has one end attached cantilevered to a carrier, which is fashioned as a floor stand 12 that is movable on the wheels 11. Due the movability of the gantry 1 on the rails 7 and due the movability of the support table 9 on the wheels 11 of its floor stand 12, longitudinal displaceability of the support plate 10 relative to the floor stand 12 is not necessary, thus allowing the support plate 10 to be attached to the floor stand 12 in a non-displaceable manner.

Therefore, the support table 10 is not of a type as is conventional in computed tomography, with a support plate that can be displaced relative to a carrier. Instead, the support table 10 of the inventive apparatus has a significantly simpler structure which, due to the cantilevered support plate 10, enables the placement of the gantry 1 into a use position corresponding to the type of examination so that the support plate 10 extends through the measuring opening 3. For this purpose, it is only necessary to place the support table 9 coarsely in such a position, so that an area of the patient that is to be examined can be reached by adjusting the gantry 1 on the rails 7.

Due to the motor-driven adjustability of the gantry 1 in the direction of the system axis Z, there is also the possibility of undertaking volume scans of a relevant examination area of the patient. In a known manner, such volume scans can be carried out as sequence scans or as spiral scans. In the case of sequence scanning, a stepped displacement of the gantry 1 in the direction of the system axis Z ensues after scanning of a planar slice of the examination area until the relevant examination area is scanned in the form of a sequence of planar slices. In the case of a spiral scan, the rotary ring 3 rotates continuously, while the gantry 1 is continuously mixed in the direction of the system axis Z, whereby the rotating speed of the rotary ring 3 and the translational speed of the gantry 1, in the direction of the system axis Z, have a fixed ratio to one another corresponding to the desired pitch of the spiral scan.

Figure 2:
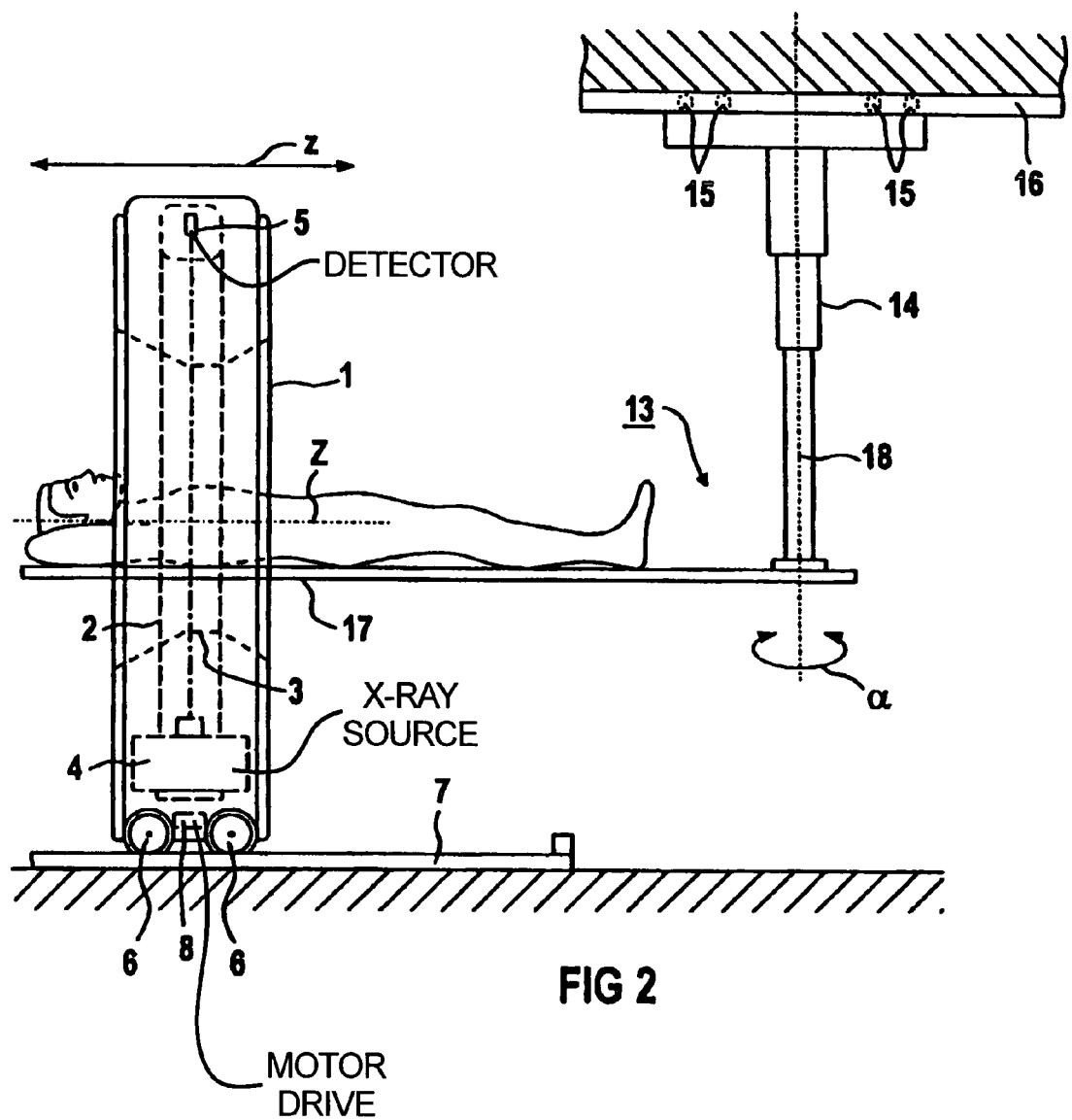
FIG. 2 is a view from above of a further embodiment of an inventive computed tomography apparatus.

The computed tomography apparatus shown in FIG. 2 differs from the embodiment of FIG. 1 in that the support table 13 has a ceiling stand 13 as a carrier for the support plate 17. The ceiling stand 13 can be moved by rollers 14 always two parallel ceiling rails 15 (only one is visible in FIG. 2).

Analogously to the previously described exemplary embodiment, the support plate 17 of the support table 13 in the embodiment of FIG. 2 is attached to the ceiling stand 14 in a non-displaceable manner, however, there is the possibility to pivot the bearing plate 17 around the center axis 18 of the ceiling stand 14 in the direction of the curved double arrow a.

Figure 3:
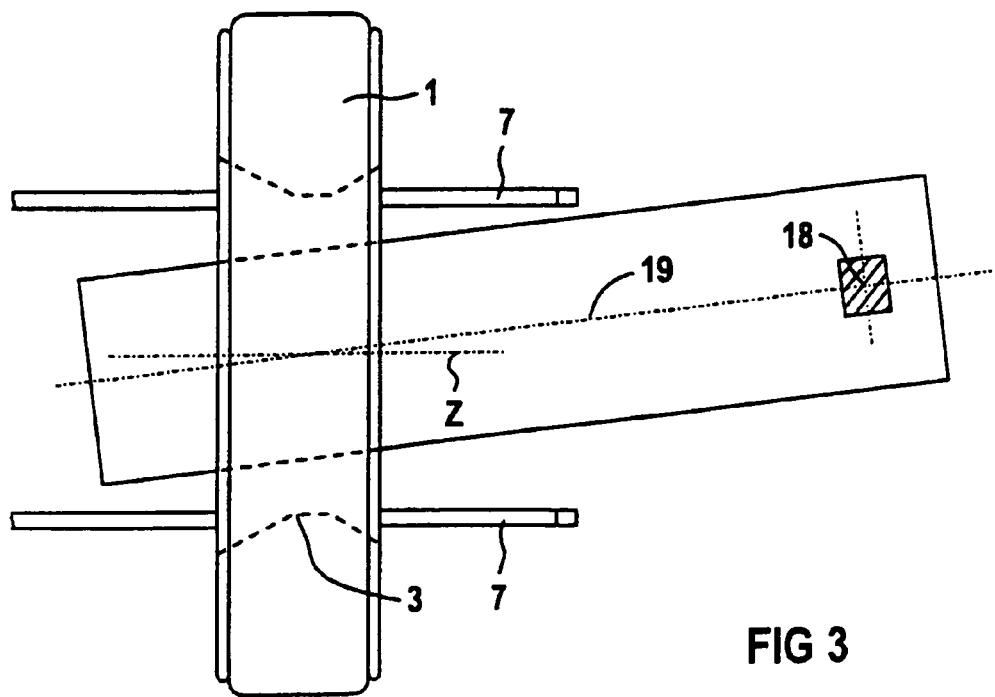
FIG. 3 is a side view showing a particular operational condition of the computed tomography apparatus according to FIG. 2.

As shown in FIG. 3, it is therefore possible to conduct examinations with swivel, wherein the support table 13 and the gantry 1 are positioned relative to one another such that the straight lines cross (intersect), which are respectively generated by parallel projections of the longitudinal axis 19 of the support plate 17 and the system axis in a horizontal plane, for example, on the floor of the examination room when the gantry 1 (as shown in FIG. 3) is in a use position in which the support plate 17 extends through the measuring opening 3 of the gantry 1.

In the exemplary embodiment according to FIG. 1, the support table 9 and the gantry 1 can be positioned relative to one another such that examinations with swivel are possible.

The fashioning of the support tables 9 and 13 in the described exemplary embodiments is only an example. The important feature of the inventive apparatus is that the support table 9 or 13 is constructed such that the gantry 1 can be moved into a use position in which the plate 10 or 17 extends through the measuring opening of the gantry 1.

In the exemplary embodiments, only one support table 9 or 13 is shown. In the context of the invention, however, a number of support tables can be provided in order to be able to prepare a number of patients at the same time in the interest of an optimal use of the computed tomography apparatus, so that examinations of the individual patients can ensue immediately in succession.

The invention can be used in computed tomography apparatuses with a single-line detector, a multiple-line detector or a matrix-like detector.

The computed tomography apparatuses according to the described exemplary embodiments are computed tomography apparatuses of the third generation, however, the invention can be used with computed tomography apparatuses of the fourth generation as well.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus comprising:
    a gantry having a measuring opening and a system axis;
    an x-ray source mounted in said gantry having a focus from which radiation is emitted, at least said focus rotating around said measuring opening for irradiating an examination subject from different directions;
    a detector disposed in said gantry facing said opening for obtaining projection datasets corresponding to radiation incident on said detector as said focus rotates around said measuring opening;
    a support table having a continuous, one-piece support plate, having a length along a longitudinal axis of the support plate adapted to receive an entirety of an examination subject thereon, and a carrier, said support plate being non-displaceably mounted cantilevered to said carrier; and
    a mechanism for moving said gantry independently of said support table, including movement of said gantry into a use position wherein said support plate extends through said measuring opening and wherein said support plate is positioned relative to said gantry so that said longitudinal axis and said system axis, when projection into a horizontal plane, intersect.

2. A computed tomography apparatus as claimed in claim 1 wherein said carrier comprises a floor stand.

3. A computed tomography apparatus as claimed in claim 1 wherein said carrier comprises a ceiling stand.

4. A computed tomography apparatus as claimed in claim 1 wherein said support table is movable.

5. A computed tomography apparatus as claimed in claim 1 wherein said gantry has a system axis and further comprising a motor drive for moving said gantry along said system axis to allow scanning of a volume of an examination subject adapted to be received on said support plate in said measuring opening.

6. A computed tomography apparatus as claimed in claim 1 wherein said mechanism comprises rails along which said gantry is movable.

* * * * *